United States Patent [19]

Rizzo et al.

[11] Patent Number: 4,987,307
[45] Date of Patent: Jan. 22, 1991

[54] INTRABUCCAL DETECTOR FOR X-RAY APPARATUS

[75] Inventors: Giorgio Rizzo, Milan; Giuseppe Cilia, Novara; Cesare Gadda, Pregnana Milanese, all of Italy

[73] Assignee: Fiad S.P.A., Trezzano Sul Naviglio, Italy

[21] Appl. No.: 423,818

[22] Filed: Oct. 18, 1989

[30] Foreign Application Priority Data

Oct. 21, 1988 [IT] Italy .................................. 22394 A/88
Jul. 20, 1989 [IT] Italy .................................. 21245 A/89

[51] Int. Cl.⁵ .......................... G01T 1/20; A61B 6/14
[52] U.S. Cl. .............................. 250/368; 250/370.09; 250/370.11; 378/191
[58] Field of Search ............. 250/368, 370.09, 370.11; 378/99, 191, 62; 358/111

[56] References Cited

U.S. PATENT DOCUMENTS 3,622,785 11/1971 Lewis et al. .................... 378/191
4,878,234 10/1989 Pfeiffer et al. ............... 250/370.09

FOREIGN PATENT DOCUMENTS 0285214 3/1988 European Pat. Off. ........... 378/191

Primary Examiner—Janice A. Howell
Assistant Examiner—Drew A. Dunn
Attorney, Agent, or Firm—Browdy and Neimark

[57] ABSTRACT

An intrabuccal detecotr for X-ray apparatus is provided which comprises an outer containment enclosure (10), a scintillation screen (13) adapted to convert X-radiation to light signals, a CCD sensor (16) adapted for converting the light signals to electric signals, and an optical system (15) between the scintillation screen (13) and the CCD sensor (16) which includes a plurality of microlenses (15a) adapted for concentrating the light signals from the scintillation screen (13) onto the CCD sensor (16).

12 Claims, 4 Drawing Sheets

INTRABUCCAL DETECTOR FOR X-RAY APPARATUS

BACKGROUND OF THE INVENTION

The invention has for its subject-matter an intrabuccal detector for X-ray apparatus of the kind employed in stomatology.

As is known, the most advanced X-raying techniques have been using since long stomatologic X-ray apparatus which comprise an intrabuccal detector or sensor responsive to X-radiation from an external source, a signal processing unit connected by a cable to the intrabuccal detector or sensor, and a device connected to the processing unit and capable of displaying the X-ray picture received by the detector.

Studies constantly directed to improving this radiological technique have shown that the cited intrabuccal detector or sensor is de facto the most important element in the apparatus in question in that it affects most their functionality.

In fact, whereas the other parts of such apparatus can be designed unrestrictedly because external to the patient and possibly located away from the X-ray source, the detector must be provided quite small in order to fit in the patient's mouth in a plurality of positions.

In addition, the intrabuccal detector is the single source of the imaging signals sent to the processing unit, and accordingly, if its resolutive power is poor, the processing unit will be unable to produce adequately sharp pictures, regardless of how powerful the unit may be.

It should be also considered that the intrabuccal detector is not only to output signals to the processing unit but also to itself process said signals in part, in order for the latter to be transmitted over a preferably long and thin cable that causes no inconvenience for the patient.

Also, tied to the responsiveness of the intrabuccal detector or sensor is the strength of the radiation to be emitted by the X-ray source, and it is essential that such radiation strength be as low as possible not to be harmful for the patient in view of that several radiographs of the mouth may be necessary in some cases.

The most widely used of known intrabuccal detectors employs two elements, namely: a scintillation screen adapted to convert at least in part X-radiation into visible light, and a CCD (Charge Coupled Device) sensor responsive to the light emission from the scintillation screen and capable of converting the same to electric signals.

CCD sensors are highly expensive and are generally small in size, whilst scintillation screens are much cheaper and must have large dimensions equal to those of the mouth region to be radiographed.

Thus, there exists the problem of how to relate the broad surface of the screen to a smaller surface area of the CCD sensors.

It has been known, in an attempt at solving this problem, to guide and convey the light beam from the scintillation screen to the CCD sensor by means of fiber optics set to converge.

According to this prior approach, the fiber optics are tapered and have a large cross-sectional area end in contact with the scintillation screen and a small cross-sectional area end in contact with the CCD sensor.

The approach just described is in many ways less than fully satisfactory.

First, the extent of the convergence and concentration of the light rays to be obtained by guiding them with tapering fiber optics is quite modest. This because it is impossible to provide fiber optics having greatly different end cross-sectional areas, both on account of that the small section ends cannot be made thin beyond certain limits in practice and above all that the large section ends must be also made very thin to avoid that the CCD sensor may be transmitted too coarse a picture.

In fact, fiber optics have unavoidable interstices between fibers, which interstices become enhanced as the fiber cross-section increases. The generally circular cross-sectional shape of fiber optics makes then unacceptable bundling together relatively large cross-section fibers.

A small amount of convergence is unsatisfactory not only because it reduces the detector bulk by a minor amount and only slightly improves the picture brightness at the CCD sensor, but above all because it attenuates in no significant way the strength of the X-radiation delivered to the patient and the scintillation screen due to the resulting low increase in brightness.

Another drawback is that the arrangement of fiber optics between the screen and the sensor restricts the extent of the image processing which can be applied downstream from the intrabuccal detector: in particular, the images can only be slightly enlarged because fiber optics, albeit thin, transmit a blurred image, i.e. a point or spot one. This drawback defeats in part the possibility of having highly sophisticated electronic units arranged downstream from the detector.

A further drawback is that if the screen is linked to the sensor through said fiber optics, a detector is provided wherein the screen-fiber-sensor assembly is difficult to set up, wherein no room is allowed for any additional elements such as internal filters and the like, and wherefrom heat cannot be readily dissipated but is transferred directly by conduction to the various elements.

Thus the technical problem remains unsolved of how to make the relatively large picture on the scintillation screen to converge efficiently into a high-performance small-size CCD sensor with respect to said screen.

SUMMARY OF THE INVENTION

This being the situation, the technical task that underlies this invention is to provide an intrabuccal detector which can substantially solve said technical problem.

Said technical task is substantially performed by an intrabuccal for X-ray apparatus comprising: an outer containment enclosure, a scintillation screen adapted to convert emitted X-rays to light signals, a CCD sensor adapted to convert said light signals to electric signals, and being characterized in that it comprises an optical system placed between said scintillation screen and said CCD sensor and including a plurality of micro-lenses adapted to concentrate said light signals from said scintillation screen onto said CCD sensor.

BRIEF DESCRIPTION OF THE DRAWINGS

Further features and the advantages of the invention will become apparent from the following detailed description of two preferred embodiments of an intrabuccal detector, to be read in conjunction with the accompanying drawings, where.

DETAILED DESCRIPTION OF THE INVENTION

Figure 1:
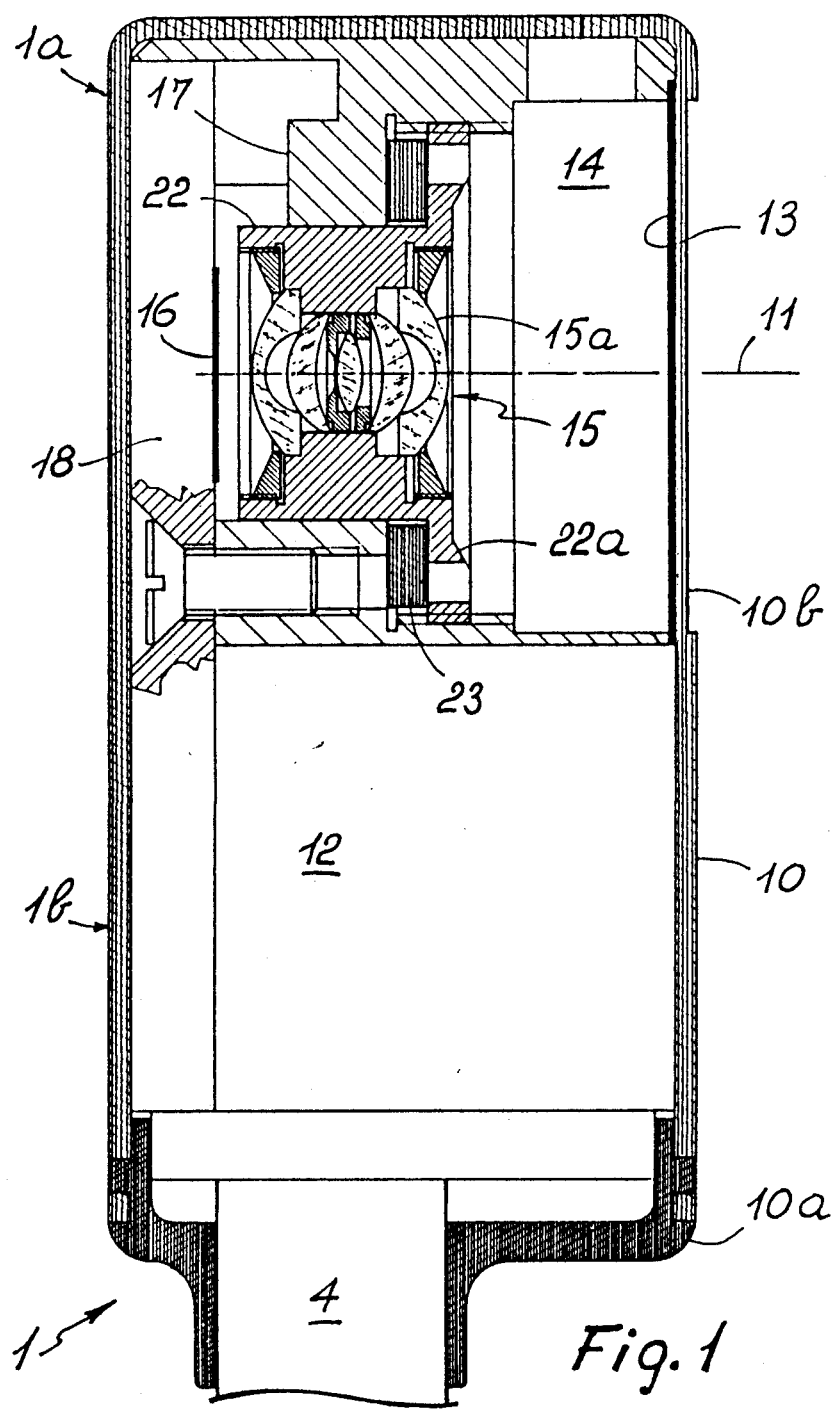
FIG. 1 is a general cross-sectional view showing schematically and to a much enlarged scale an intrabuccal detector according to the invention.

With reference to the cited drawing figures, the intrabuccal detector or sensor of this invention is generally denoted by the numeral 1. It is part of an X-ray apparatus 2 shown in FIG. 6 by way of example and comprising, besides the detector 1, a processing unit 3 connected to the detector 1 by means of a cable 4, a keyboard 5 and monitor 6 connected to the processing unit 3, and a printer 7 capable of reproducing the pictures being displayed on the monitor 6.

Figure 6:
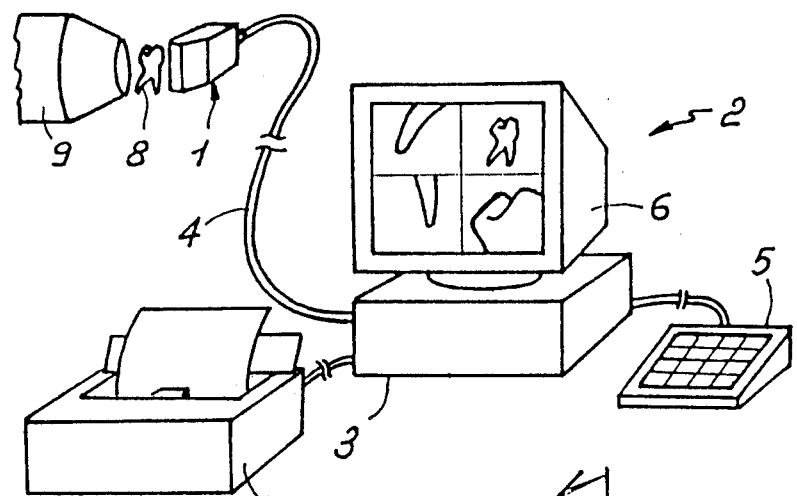
FIG. 6 shows an X-ray apparatus incorporating the detector of this invention.

Shown apart in FIG. 6 is a tooth 8 flanked on one side by a portion of the detector 1 and on the other side by an X-ray source 9. The tooth 8 image is displayed on the monitor 6 which also shows certain processings of that image consisting of magnified details of the tooth 8.

The intrabuccal detector 1 of this invention has a containment enclosure 10 extending all over its outer surface which has a main dimension crosswise, in the working position, to the direction of propagation of the X-rays, and a small lid 10a at the cable 4.

The enclosure 10 is light-opaque throughout and preferably opaque to X-radiation as well, with the exception of a pick-up zone 10b parallel to said main dimension of the enclosure 10.

Two basic zones are distinguishable inside the detector: a first zone 1a extending adjacent a first symmetry axis 11 of the pick-up zone 10b, which is substantially aligned to the X-ray source 9, and a second zone 1b beside the first which contains among others an output signal driver 12. This driver 12 is preferably a hybridized driver which processes initially said signals so as to permit, among others, of a remote location of the processing unit 3.

The first zone 1a is engaged, directly inside the pick-up zone 10b of the enclosure 10, by a planar scintillation screen 13 having the first symmetry axis 11 for its symmetry axis.

The scintillation screen 13 is, within the enclosure 10, adjacent an opening 14 contiguous to an optical relay or optical system 15 comprising micro-lenses 15a and fitting between the scintillation screen 13 and a CCD sensor 16.

The scintillation screen 13 is known per se and to a design adapted for converting the X-radiation from the source 9 to light signals having a predetermined wavelength.

The scintillation screen 13 is envisaged mounted at a location directly adjacent the enclosure 10. In order for the location of the scintillation screen 13 to be recognized from outside, the enclosure 10 is formed with a sunk area 10b at the screen location.

The CCD sensor 16, also referred to as charge coupled device or array, is adapted to convert light signals to electric signals, and is preferably selected to have a high resolutive power. It is located away from the scintillation screen 13 and is much smaller in size than the screen.

The optical relay or optical system 15 is advantageously adapted to concentrate onto the CCD sensor 16 all the light signals output by the scintillation screen 13 and is separated from both the scintillation screen 13 and the sensor 16, but closer to the latter.

Figure 2:
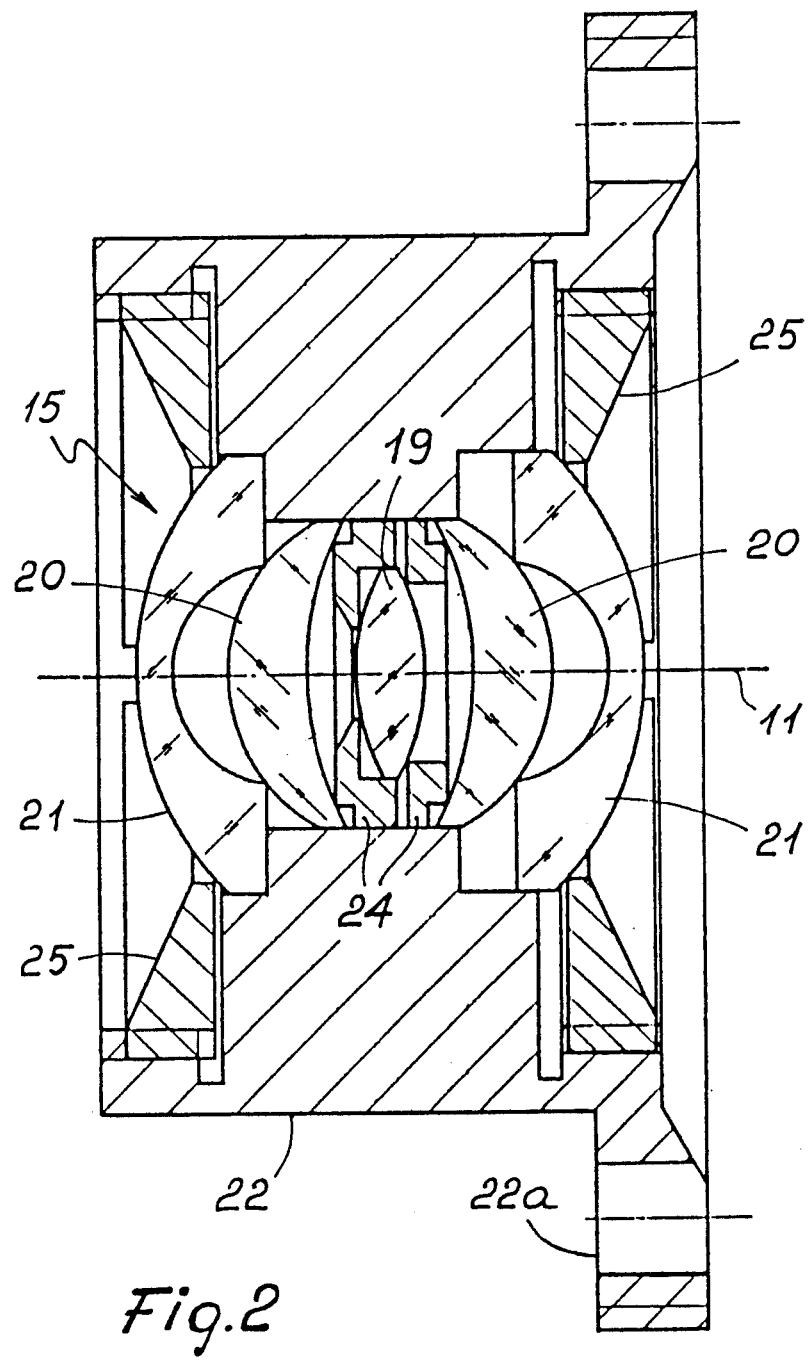
FIG. 2 shows a portion of the preceding figure further enlarged and set apart.

In the embodiment shown in FIGS. 1 and 2, the optical system 15 is facing directly the scintillation screen 13 and has the first symmetry axis 11 for its symmetry axis.

The optical system 15 fits inside a rigid body 17 opaque to X-radiation, and the CCD sensor 16 lies parallel to the scintillation screen 13, it being engaged with a base 18 which extends into the second zone 1b. FIG. 2 shows in particular that the optical system 15 is of a symmetrical type with a wide field angle technically recognizable by the term "double-Gauss", and is formed of micro-lenses 15a aligned along the first axis 11 of symmetry.

In detail, the optical system of FIGS. 1 and 2 is formed of five micro-lenses 15a including: a convex-convex center micro-lens 19, two concave-convex converging meniscus micro-lenses 20 flanking the convex-convex center micro-lens 19 on opposite sides thereof, and two convex-concave diverging meniscus micro-lenses 21 located at the ends of the optical system 17.

All the micro-lenses 15a are made from known "optical glass" having a high lead content and being therefore opaque to X-ray. In addition, all the micro-lenses 15a fit in a holder 22, such as an aluminum barrel, which is opaque to X-ray and independent of the scintillation screen 13 and the CCD sensor 16. The holder 22 has a flange-like enlargement 22a which engages as by threading with the body 17. The threads on the body 17 for threadably receiving the flange 22a is concentrical with the first symmetry axis 11.

Advantageously between the flange 22a and the body 17 there intervenes an elastic means 23, e.g. a rubber ring.

We also point out that in the holder 22 the micro-lenses 15a engaged by means of inside spacers 24 and locking ring nuts 25 at the ends, as shown in FIG. 2. The locking ring nuts 25 are threaded to the holder 22.

Figure 3:
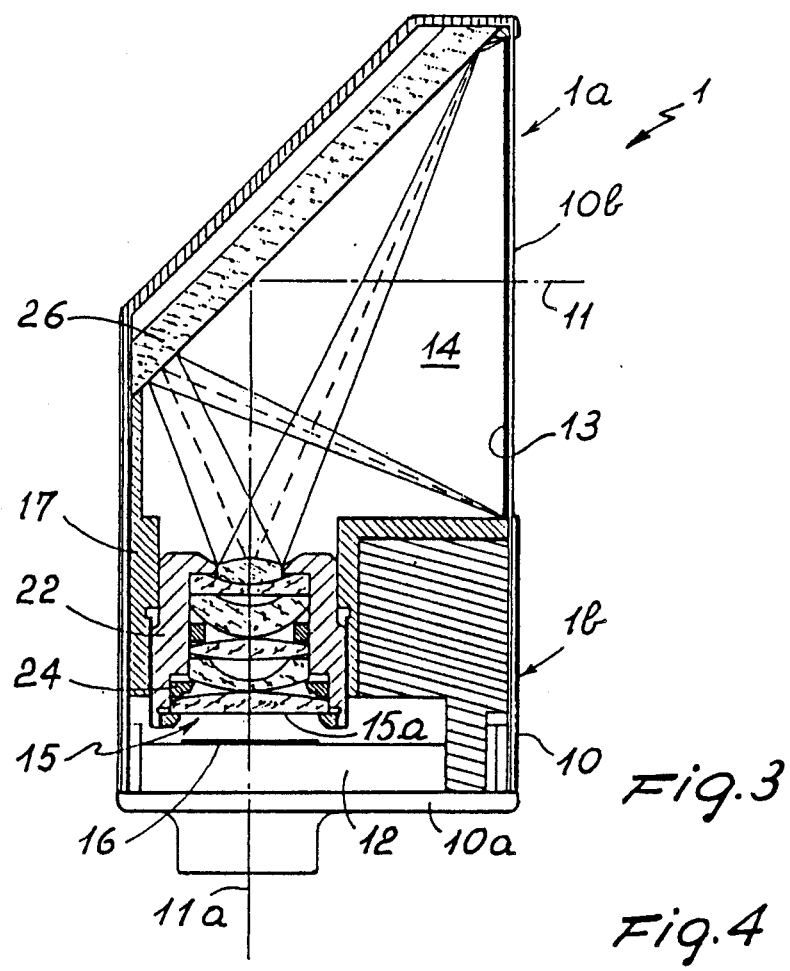
FIG. 3 is a general enlarged and schematic cross-sectional view of another intrabuccal detector according to the invention.
Figure 4:
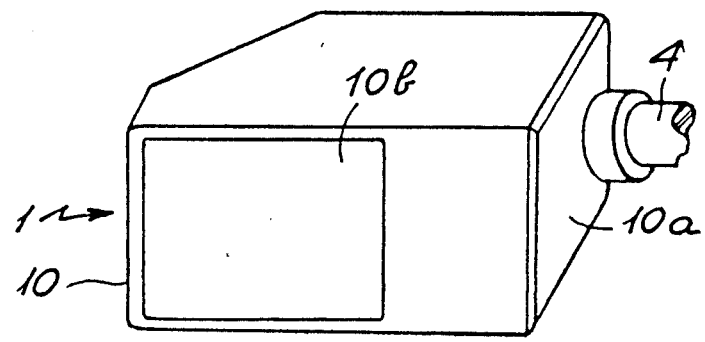
FIG. 4 shows the exterior of the detector of FIG. 3.
Figure 5:
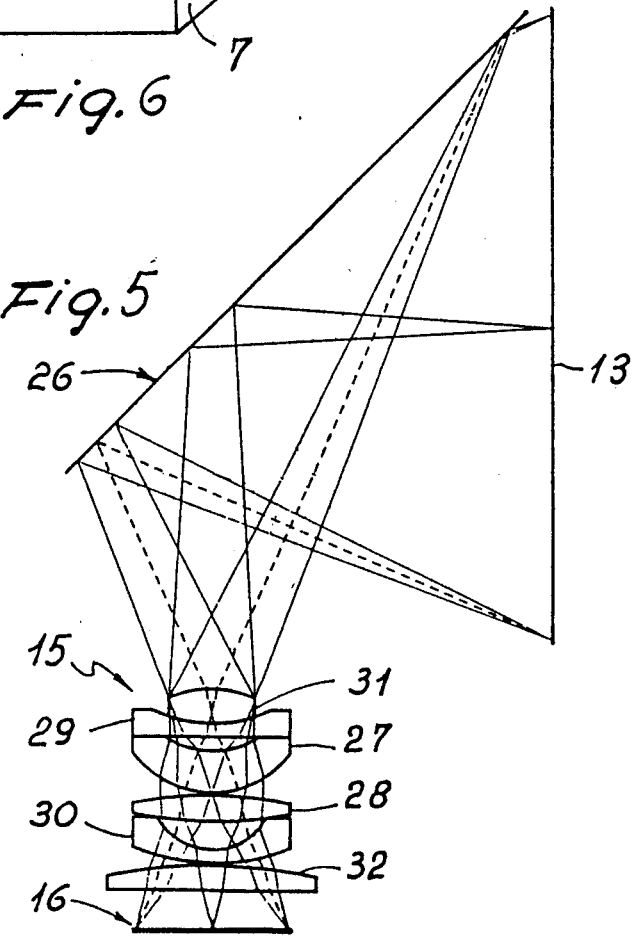
FIG. 5 shows the optics of FIG. 3 to a further enlarged scale and set apart.

In the embodiment shown in FIGS. 3, 4 and 5, provided adjacently the scintilation screen 12 is a reflective element 26 defined by a substantially planar mirror set at an angle of 45e to the scintillation screen 13.

The body 17 housing the holder 22 which contains the micro-lenses 15a of the optical system 15 and the spacers 24, fits into the second zone 1b, and the optical system 15 has a second symmetry axis 11a parallel to the scintillation screen 13 and above all to said main dimension of the enclosure 10.

The holder 22, consisting of an aluminum barrel, is engaged as by threading with the body 17 and the threads are concentric with the second symmetry axis 11a.

The CCD sensor 16 locates on the opposite side from the reflective element 26 and has the same symmetry axis as the optical system 15. Both the optical system 15 and the CCD sensor 16 contained in the second zone 1b are placed outside the flow cone of X-rays which sweeps the scintillation screen 13. It is envisaged that the overall path of each of the light signals output by the scintillation screen 13 be defined by a first section extending between the scintillation screen 13 and the reflective element 26, and a second reflected section included between the reflective element 26 and the optical system 15.

Altogether, said general path extends over a longer distance than the breadth of the enclosure 10 in the direction of the first center symmetry axis 11 orthogonal to the scintillation screen 13.

The optical system 15, effective to concentrate all the light signals being re-directed by the reflective element 26 onto the CCD sensor 16, is of an asymmetrical type with a small field angle, e.g. of 60°, and the micro-lenses 15a are aligned along the second symmetry axis 11a. The small field angle is made possible by the provision of said relatively broad general path of the light signals, as brought about by the reflective element 26.

As shown in FIG. 3, there are six micro-lenses 15a of which one is an additional lens placed close to the CCD sensor 16.

In detail (FIG. 5), optical system comprises centrally a first converging meniscus concave-convex micro-lens 27 and a first convex-convex micro-lens 28 in mutual contact with their convex sides.

Also provided, on opposite sides from these center micro-lenses, are a plano-concave micro-lens 29 having its planar side facing the concave side of the first concave-convex micro-lens 27, and a second diverging meniscus concave-convex micro-lens 30 with its concave side facing the first convex-convex micro-lens 28. Lastly, there are a second convex-convex micro-lens 31 mating outwardly with the plano-concave micro-lens 29, and said additional micro-lens consisting of a plano-convex micro-lens 32 having its convex side in contact with the second concave-convex micro-lens 30.

The detector operates as follows.

Under a working condition, the intrabuccal detector 1 is introduced into the patient's mouth with the sunk area 10b, and hence the scintillation screen 13, facing the part to be radiographed, e.g. a tooth 8 and adjacent gum.

The X-ray source 9 is positioned perpendicularly to the part to be radiographed and the sunk area 10b outside the mouth, and an emission of X-rays is initiated. The radiation will travel through the mouth part to be radiographed generating dark and bright spots making up the X-ray picture, and impinge on the scintillation screen 13 after also going through the sunk area 10b of the enclosure 10.

The scintillation screen 13 converts the X-radiation to light signals for the CCD sensor 16.

In the embodiment of FIGS. 1 and 2, on exiting the scintillation screen 13, the light beam is at once strongly concentrated by the micro-lenses 15a of the optical system 15 to produce on the CCD sensor 16 a much smaller picture than that of the scintillation screen 15.

In the embodiment of FIGS. 3,4,5, the light beam will first impinge on the reflective element 26 which divert them over a relatively long distance. The optical system 15 requires therefore a relatively small field angle.

The CCD sensor 15 will then convert the light signals to electric signals, and the latter, following processing in the driver 12, are sent over the cable 4 to the processing unit 3 and thence to the monitor 6 and possibly the printer 7, as shown in FIG. 6.

The invention affords important advantages.

The provision of the optical system 15 with micro-lenses 15a allows, within the intrabuccal detector 1, of a strong convergence and concentration of the light beam, which results in a picture of increased brightness and the possibility for attenuating the intensity of the X-radiation. The demagnification of the image may be selected as desired within limits, without pre-arranged a priori limitations.

The whole image is processed by the optical system 15, with no break zones. In addition, with a micro-lens 15a optical system of the kind described above, the image sent to the processing unit 3 is particularly sharp and may be liberally processed at high magnifications.

Another advantage of the inventive detector is that it has minimum bulk dimensions smaller than those of currently known detectors.

These results have been obtained with an "open" structure: the optical system 15 can easily mounted without interfering with the scintillation screen 13 and the CCD sensor 16, and in the proximities of the same there are still left large spaces to accommodate, where required, such auxiliary elements as additional filters.

The X-radiation impinging on the detector is either fully converted to light signals or arrested, to prevent it from reaching the CCD sensor or travelling once again through the patient. In fact, the entire mechanical structure inside the detector is opaque to X-radiation and the micro-lenses 15a are opaque to X-radiation.

The embodiment of FIGS. 1 and 2 has to a high degree the quality of being extremely compact and simple, whilst the embodiment of FIGS. 3 to 5 has the advantage that the distance between the reflective element 26 and the optical system 16 is relatively long and freely increasable during the designing stage, there being no space problems for the intrabuccal detector 1 along its main dimension parallel to the second symmetry axis 11a.

It is therefore possible to use an optical system with a reduced field angle, which enables the brightness of the picture to be uniform throughout without significant variations from the center out. In actual practice, one can move from an optical system with a field angle of about 140°, with the micro-lenses 15a aligned directly to the scintillation screen 13, to an optical system with a field angle of about 60°, where the light beam is redirected by the reflective element 26. It follows that less expensive and more image-wise more efficient optical systems can be used.

We claim:

1. An intrabuccal detector for X-ray apparatus, comprising: an outer containment enclosure (10), a scintillation screen (13) adapted to convert emitted X-rays to light signals, a CCD sensor (16) adapted to convert said light signals to electric signals, and comprising an optical system (15) placed between said scintillation screen (13) and said CCD sensor (16) and including a plurality of micro-lenses (15a) adapted to concentrate said light signals from said scintillation screen (13) onto said CCD sensor (16).

2. An intrabuccal detector as in claim 1, wherein said optical system (15) is located away from both said scintillation screen (13) and said CCD sensor (16).

3. An intrabuccal detector as in claim 1, wherein a holder (22) for said optical system (15) is provided within said enclosure (10) interposed between said scintillation screen (13) and CCD sensor (16) and being positionable within said enclosure independently of said scintillation screen (13) and CCD sensor (16).

4. An intrabuccal detector as in claim 3, wherein a rigid body (17) opaque to X-radiation is provided within said enclosure (10); wherein said holder (22) is rigid and opaque to X-radiation and engaged with said body (17) as by threading, said threading taking place in a coaxial direction with said CCD sensor (16); and wherein said micro-lenses (15a) housed in said holder (22) are made of optical glass opaque to X-radiation.

5. An intrabuccal detector as in claim 1, wherein a first symmetry axis (11) is provided which is substantially central and orthogonal to said scintillation screen (13), and wherein said optical system (15) and said CCD sensor (16) are coaxial with said first symmetry axis (11).

6. An intrabuccal detector as in claim 5, wherein said optical system (15) is symmetrical and has a wide field angle and comprises a convex-convex center micro-lens (19), two concave-convex micro-lenses (20) which are diverging meniscus-shaped and flank on opposite sides said convex-convex center micro-lens (19) and two convex-concave micro-lenses (21) diverging meniscus-shaped which locate at opposite ends of said optical system (15).

7. An intrabuccal detector as in claim 1, wherein between said scintillation screen (13) and said optical system (15) is a reflective element (26), said reflective element (26) being adapted to divert said light signals from said scintillation screen (13) to said optical system (15).

8. An intrabuccal detector as in claim 7, wherein each said light signal has an overall path comprising a first section extending between said scintillation screen (13) and said reflective element (26), and a second section at an angle to said first section which extends between said reflective element (26) and said optical system (15), said overall path being longer than the breadth of said enclosure (10) orthogonally to said scintillation screen (13).

9. An intrabuccal detector as in claim 7, wherein said enclosure (10) has a first symmetry axis (11) which is substantially central and orthogonal to said scintillation screen (13), and a main dimension crosswise to said first symmetry axis (11), and wherein said optical system (15) has a second symmetry axis (11a) substantially parallel to said main dimension.

10. An intrabuccal detector as in claim 7, wherein said reflective element (26) is defined by a substantially plane mirror set at an angle of substantially 45° to said scintillation screen (13).

11. An intrabuccal detector as in claim 7, wherein said optical system (15) has a reduced field angle and comprises a first concave-convex micro-lens (27) substantially centrally located and converging meniscus-shaped, a first convex-convex micro-lens (28) and a first plano-concave micro-lens (27) in contact on opposite sides with said first concave-convex micro-lens (27), a second concave-convex micro-lens (30) diverging meniscus-shaped in contact with said first convex-convex micro-lens (28), and a second convex-convex micro-lens (31) in contact with said first plano-concave micro-lens (29) and forming one end of said optical system (15) facing said reflective element (26).

12. An intrabuccal detector as in claim 11, wherein a plano-convex micro-lens (32) is also provided in contact with said second concave-convex micro-lens (30) and forming one end of said optical system (15) facing said CCD sensor (16).

* * * * *